United States Patent [19]

Grigoleit et al.

[11] 4,357,472

[45] Nov. 2, 1982

[54] PROCESS FOR THE PRODUCTION OF THIONAPHTHENE FROM THIONAPHTHENE SULFONIC ACID

[75] Inventors: Georg Grigoleit, Dorsten; Kurt Matern, Duisburg; Helmut Köhler, Mülheim an der Ruhr; Gerd Collin, Duisburg, all of Fed. Rep. of Germany

[73] Assignee: Rutgerswerke Aktiengesellschaft, Frankfurt am Main, Fed. Rep. of Germany

[21] Appl. No.: 219,172

[22] Filed: Dec. 22, 1980

Related U.S. Application Data

[63] Continuation-in-part of Ser. No. 946,892, Sep. 28, 1979, abandoned.

[30] Foreign Application Priority Data

Sep. 30, 1977 [DE] Fed. Rep. of Germany ....... 2744066

[51] Int. Cl.$^3$ ............................................. C07D 333/54
[52] U.S. Cl. ....................................................... 549/49
[58] Field of Search ........................................... 549/49

[56] References Cited

U.S. PATENT DOCUMENTS 4,098,838  7/1978  Grigoleit .............................. 549/49

FOREIGN PATENT DOCUMENTS 325712  7/1919  Fed. Rep. of Germany ........ 549/49
333156  2/1921  Fed. Rep. of Germany ........ 549/49

*Primary Examiner*—Henry R. Jiles
*Assistant Examiner*—Robert C. Whittenbaugh
*Attorney, Agent, or Firm*—Beveridge, DeGrandi & Kline

[57] ABSTRACT

A process for the production of thionaphthene by dissociation of thionaphthene sulfonic acid such as obtained, for example, in the partial sulfonation of naphthalene fractions of coal tar, characterized in that the density of the reaction mixture is maintained essentially constant during the entire duration of the dissociation reaction and the thionaphthene formed is not removed by azeotropic distillation; a product of high purity is obtained in high yield in a substantially reduced reaction time.

11 Claims, No Drawings

PROCESS FOR THE PRODUCTION OF THIONAPHTHENE FROM THIONAPHTHENE SULFONIC ACID

This application is a continuation in part of Ser. No. 946,892, filed Sept. 28, 1979, now abandoned.

The present invention relates to a process for the production of thionaphthene by dissociation of thionaphthene sulfonic acid as obtained for example, in the partial sulfonation of naphthalene fractions of coal tar (cf. Franck and Collin, Coal Tar, Springers publishers, 1968, page 72).

From German AS No. 25 35 192, it has been known to isolate thionaphthene from corresponding tar oil fractions by partial sulfonation and subsequent dissociation of the sulfonic acid mixture that developed with superheated steam. Thionaphthene which is obtained in accordance with this process at temperatures of about 120° to 140° C. in 70%–80% concentration, is obtained in pure form in an additional cleaning step by distillation and crystallization.

For obtaining thionaphthene on an industrial scale, however, this process is not particularly suitable since the dissociation process is exceedingly time consuming and wasteful and thus leads to considerable costs. As a result, the fields of application for thionaphthene and its derivatives have not, up to the present, reached practical significance (cf. Franck and Collin, supra, page 183).

It is therefore an object of the present invention to find a new process for obtaining thionaphthene by dissociation of thionaphthene sulfonic acid which may be carried out at an industrial scale and which is based on a simple and economical method. This object is solved by the process according to the present invention.

Still further objects and the entire scope of applicability of the present invention will become apparent from the detailed description given hereinafter; it should be understood however, that the detailed description and specific examples, while indicating preferred embodiments of the invention, are given by way of description only, since various changes and modifications within the spirit and scope of the invention will become apparent to those skilled in the art therefrom.

The object is attained by the present invention which is a process for the production of thionaphthene from thionaphthene sulfonic acid by dissociation with water, characterized in that during the entire period of the reaction, the density of the reaction mixture is maintained essentially constant and the thionaphthene formed is not removed by azeotropic distillation. That is to say, the thionaphthene formed is maintained within the reaction mixture by not carrying out a simultaneous azeotropic steam distillation.

The process of the present invention should not be confused with a thermal treatment in a closed system e.g. boiling the reaction mixture under refluxing. As the comparative examples hereinafter will show, a thermal treatment of an aqueous solution of thionaphthene sulfonic acid will result in a high yield of waste products. It is part of the present invention which the inventors herein have discovered, that this is caused by the high concentration of sulfuric acid, formed during the decomposition of the thionaphthene sulfonic acid according to the following scheme:

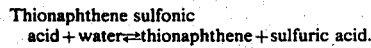

This sulfuric acid will increase the density of the reaction solution during the decomposition reaction by an amount of at least 0.1 [g/cm$^3$]. Another part of the present invention is the discovery that this deviation in density is not tolerable and that it is possible to reduce the production of waste products and to increase the yield of thionaphthene by running the thermal dissociation of the thionaphthene sulfonic acid in a reaction medium where the density is held at a constant value. This is achieved by a controlled addition of water to the reaction solution during the reaction. As a result of the controlled addition of water, the original density of the reaction mixture may be maintained essentially constant, although deviations of the density values of up to ±0.04 do not essentially influence the result.

Contrary to the hitherto customary methods of dissociation with superheated steam and with simultaneous azeotropic distillation of the thionaphthene obtained, it has been found that according to the process of the present invention, and with at least equal yields, considerably shorter reaction times are sufficient, as a result of which a process was created which can be carried out simply and on an industrial scale. When operating in an industrial scale, it has been found that when using customary steam-dissociation, on the average, for example, only about 15 kg of thionaphthene with about ten times the volume thereof of water could be dissociated per hour as azeotrope. This means that, for the dissociation of sulfonic acid and distillation to obtain one ton of thionaphthene, about 70 to 80 hours operating time were necessary. According to the process of the present invention, on the other hand, the same quantity may be obtained in a considerably shorter time (about 10 hours) since, according to this process, the time-consuming steam-distillation is omitted.

The process according to the present invention is used particularly for obtaining thionaphthene from industrial thionaphthene sulfonic acid, as may be obtained by the partial sulfonation of crude naphthalene from bituminous coal tar (e.g. according to German AS No. 25 35 192). As a result, it is possible to obtain, aside from naphthalene of the highest purity, additionally thionaphthene in a simple and industrially usable manner.

The term "reaction mixture", is to be understood an aqueous thionaphthene sulfonic acid solution such as obtained, for example, in the case of working up of the partial sulfonation of crude naphthalene (cf. German AS No. 25 35 192). Said German AS No. 25 35 192 corresponds to U.S. Pat. No. 4,098,838 issued July 4, 1978. The process is carried out preferably in the density range of 1.40 to about 1.07 [g/cm$^3$] and at a temperature of 120° to 180° C. At the same time, preferably lower reaction temperatures correspond to higher densities, and vice-versa. The preferred cited range of density corresponds to concentrations which exist in sulfonation mixtures obtained normally by partial sulfonation of crude naphthalene or which may be obtained therefrom by concentration.

The process according to the present invention may be carried out either discontinuously (batchwise) or continuously. If one operates discontinuously, the operation is conducted under reflux, preferably using densities of 1.30 to 1.40, especially 1.30 to 1.33, as a result of which temperatures of 120°–130° C. occur. On the other hand, when using the continuous method of operation the operation is conducted in a film reactor at densities of the original reaction mixtures of about 1.22 to 1.07 at temperatures between 150° and 180° C., especially 155° to 160° C.

The present invention is demonstrated in the following non-limiting examples wherein all parts are parts by weight unless otherwise specified and wherein the term "diluting liquor" signifies a 10% caustic soda solution.

amounts to 1.06. A 78% thionaphthene (solidification point 20°) is obtained at a yield of 92% of theory, which is brought to a purity of 98% by distillation and crystallization.

In a manner analogous to Example 1 or 2, results are obtained as summarized in the following table as a result of changes of the reaction conditions. In the table:

TABLE

| Starting Material | $D_4^{20}$ | Temp. (°C.) | Conditions of Cleavage Time in minutes or volume rate of the liquid ($h^{-1}$) | Thionaphthene Yield |
|---|---|---|---|---|
| RF Thionaphthene sulfonic acid-(2) Pure | 1.33 | 120 | 180 | 80.0 |
| | 1.33 | 120 | 180 | 81.8 |
| | 1.33 | 120 | 180 | 82.5 |
| | 1.33 | 125 | 60 | 71.1 |
| DS Thionaphthene sulfonic acid-(2) Pure | 1.22 | 160 | 0.7 | 81.5 |
| | 1.15 | 160 | 0.7 | 85.2 |
| | 1.15 | 155 | 0.7 | 86.1 |
| | 1.15 | 180 | 0.7 | 75.1 |
| | 1.07 | 155 | 0.7 | 79.8 |
| WD Thionaphthene sulfonic acid-(2) Pure | 1.33* | 130 | 435 | 81.9 |
| WD Thionaphthene sulfonic acid Technical | 1.33* | 130 | 480 | 83.8 |
| RF DS Thionaphthene sulfonic acid Technical | 1.33 | 125 | 90/240 | 83.8 |
| | 1.07 | 155 | 0.7 | 92.1 |
| | 1.07 | 155 | 0.7 | 91.6 |
| | 1.07 | 160 | 0.7 | 91.8 |
| | 1.07 | 180 | 0.7 | 72.9 |

*Starting values
RF signifies cleavage with reflux;
DS signifies cleavage in the film reactor; and
WD signifies steam cleavage with simultaneous azeotropic distillation, used for comparison purposes.

EXAMPLE 1

Into a reaction flask provided with a stirring mechanism, inlet tube, thermometer and reflux cooler with distillation outlet are added 100 parts of a technical thionaphthene sulfonic acid, density 1.33, as may be obtained by concentration according to the process of U.S. Pat. No. 4,098,838. After heating to 120° C., 50 parts of cold water are fed over a period of 90 minutes, while stirring. During the exothermal dissociation process, 30 parts of water are vaporized from the reaction flask and are condensed. At the end of the acid cleavage, a temperature of 125° C. has developed. The final density of the reaction mixture amounts to 1.37. After cooling down to about 30° C., the oily phase is drawn off by way of a separating vessel and is neutralized with water and diluted liquor. 83% of the theory of thionaphthene with a solidification point of 24° C. are obtained with a purity of 85%. A 98 to 99% thionaphthene is obtained through distillation and crystallization.

EXAMPLE 2

Into a perpendicularly installed film reactor provided with a heated preheating zone, wiper blade rotor and condensation receiver with a separating vessel, industrial thionaphthene sulfonic acid, as obtained according to the process disclosed in U.S. Pat. No. 4,098,838 is fed continuously by means of a feeding arrangement at a jacket temperature of the reactor of 155° to 160° C. The sulfonic acid has a density of 1.07. The liquid hourly space velocity amounts to 0.7 $h^{-1}$. The dissociation of the sulfonic acid begins almost immediately after entry into the reactor which is shown by the formation of streaks on the glass wall thereof. After leaving the reactor, the dissociated material is separated by means of a separating vessel. The lower thionaphthene phase is neutralized continuously in an extraction column with diluted liquor. The final density of the reaction mixture

EXAMPLE 3

(Comparative Example)

Into a reaction flask provided with a stirring mechanism, inlet tube, thermometer and reflux cooler with distillation outlet, are added 100 parts of a technical thionaphthene sulfonic acid, density 1.33 as may be obtained by concentration according to the process of U.S. Pat. No. 4,098,838. After heating to 120° C. without any addition of water, the exothermal dissociation process takes place within 20 minutes. The final density of the reaction mixture amounts to 1.40. After cooling down to about 30° C., the oily phase is drawn off by way of a separating vessel and is neutralized with water and diluted liquor. 58% of the theory of thionaphthene with a solidification point of 24° C. are obtained with a purity of 85%. As a by-product, a resin-like waste is obtained, namely consisting of condensation products of thionaphthene.

The comparative Example 3 was run analogous to Example 1 but without any addition of water to show that omission of water will result in a lower yield of thionaphthene, in an increase in density of the reaction mixture and an increase of undesired by-products.

What is claimed is:

1. A process for the production of thionaphthene by dissociation of thionaphthene sulfonic acid with water which comprises maintaining the density of the reaction mixture substantially constant during the entire duration of the dissociation reaction by the controlled addition of water to the reaction mixture, maintaining the thionaphthene formed within the reaction mixture by not removing said thionaphthene therefrom by azeotropic distillation, and separating thionaphthene from the reaction mixture at completion of said dissociation.

2. The process according to claim 1 wherein the reaction is conducted at a density of the reaction mixture of about 1.07 to 1.40 and a temperature of 120°–180° C.

3. The process according to claim 2 wherein the reaction is conducted at a density of the reaction mixture of 1.30–1.40 and at a temperature of 120°–130° C.

4. The process according to claim 2 wherein the reaction is conducted at a density of the reaction mixture of 1.07–1.22 and a temperature of 150°–180° C.

5. The process according to claim 4 wherein the reaction is conducted at a density of the reaction mixture of 1.07–1.22 and a temperature of 155°–160° C.

6. The process according to claim 1 wherein the reaction is conducted at a density of the reaction mixture of 1.30–1.40 and a temperature of 120°–130° C.

7. The process according to claim 1 wherein the reaction is conducted at a density of the reaction mixture of 1.07–1.22 and at a temperature of 150°–180° C.

8. The process according to claim 7 wherein the reaction is conducted at a density of the reaction mixture of 1.07–1.22 and a temperature of 155°–160° C.

9. The process according to claims 1, 2, 3, 4, 5, 6, 7, or 8 wherein the starting material is a sulfonic acid mixture obtained by partial sulfonation of naphthalene fractions of coal tar.

10. The process according to claims 1, 2, 3, 4, 5, 6, 7, or 8 wherein the reaction is carried out in a film reactor.

11. The process according to claim 10 wherein the starting material is a sulfonic acid mixture obtained by partial sulfonation of naphthalene fractions of coal tar.

* * * * *